United States Patent [19]
Farley

[11] Patent Number: 6,017,008
[45] Date of Patent: *Jan. 25, 2000

[54] CAM TIGHTENED UNIVERSAL JOINT CLAMP

[75] Inventor: Daniel K. Farley, Traverse City, Mich.

[73] Assignee: Thompson Surgical Instruments, Inc., Traverse City, Mich.

[ * ] Notice: This patent is subject to a terminal disclaimer.

[21] Appl. No.: 09/233,708

[22] Filed: Jan. 19, 1999

Related U.S. Application Data

[63] Continuation of application No. 08/482,023, Jun. 7, 1995, Pat. No. 5,897,087, which is a continuation-in-part of application No. 08/213,848, Mar. 15, 1994, abandoned.

[51] Int. Cl.[7] ................................................. A47B 96/06
[52] U.S. Cl. .................................. 248/229.21; 248/316.2
[58] Field of Search ......................... 248/229.21, 229.11, 248/228.2, 230.2, 231.31, 316.2, 541; 24/67.1, 339, 516, 540, 541; 403/84, 87, 91, 92, 97, 110; 5/503.1, 658; 606/151

[56] References Cited

U.S. PATENT DOCUMENTS

| 4,949,707 | 8/1990 | LeVahn | 128/20 |
| 5,242,240 | 9/1993 | Gorham | 403/391 |
| 5,727,899 | 3/1998 | Dobrovolny | 403/389 |
| 5,792,046 | 8/1998 | Dobrovolny | 600/234 |
| 5,888,197 | 3/1999 | Mulac | 600/234 |

*Primary Examiner*—Leslie A. Braun
*Assistant Examiner*—Gwendolyn Baxter
*Attorney, Agent, or Firm*—McAndrews, Held & Malloy, Ltd.

[57] ABSTRACT

A clamping apparatus includes a shaft member with a first clamping member and a second clamping member mounted on the shaft member. Both of the clamping members have leg portions that are movable toward and away from each other between a clamping and non-clamping position. The clamping apparatus further includes a cam member engaging the shaft member that urges the clamping members between their clamping and non-clamping positions. embodiment, the joint mechanism includes a locking mechanism for permitting quick adjustment of the joint clamp components relative to each other.

4 Claims, 11 Drawing Sheets

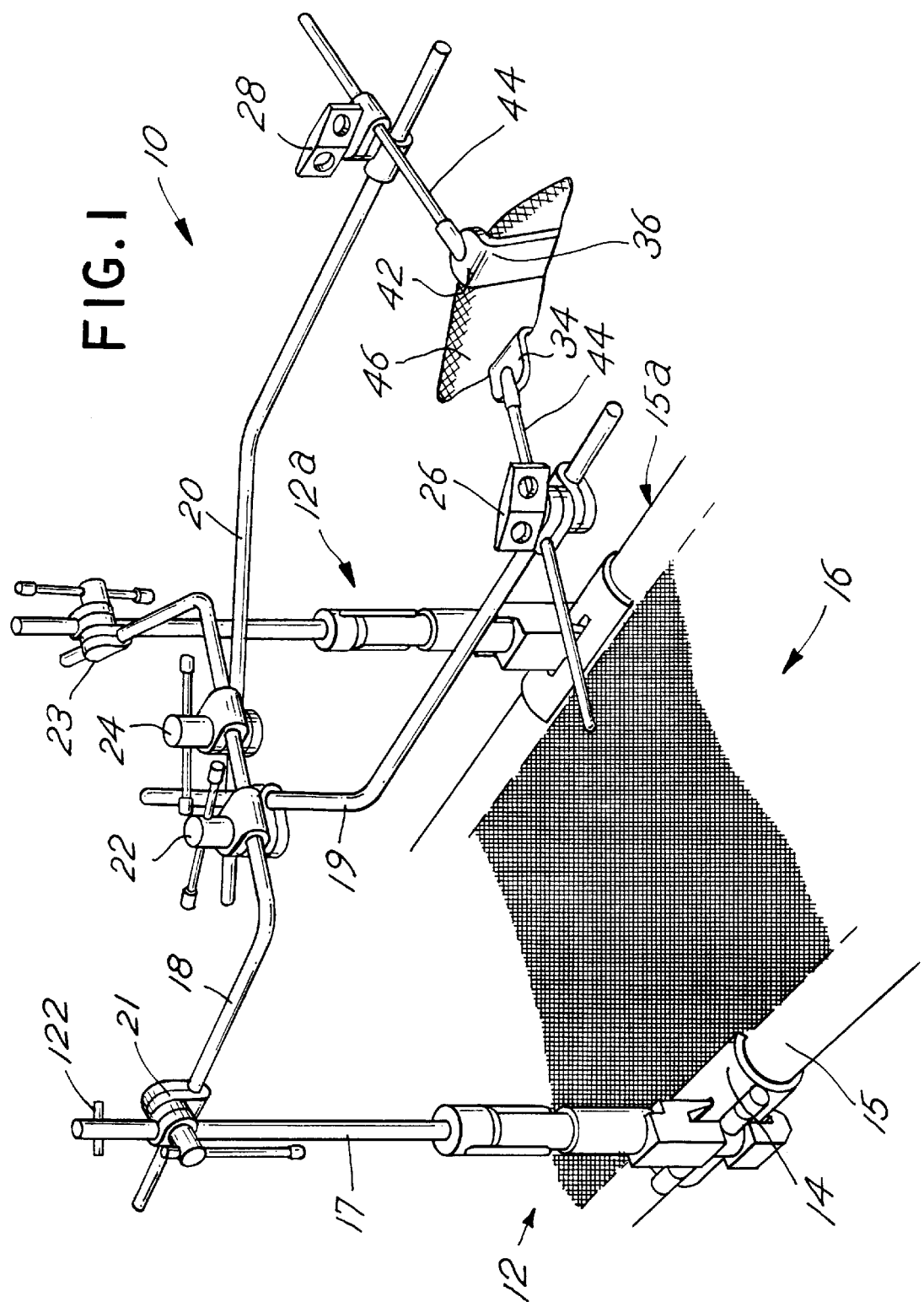

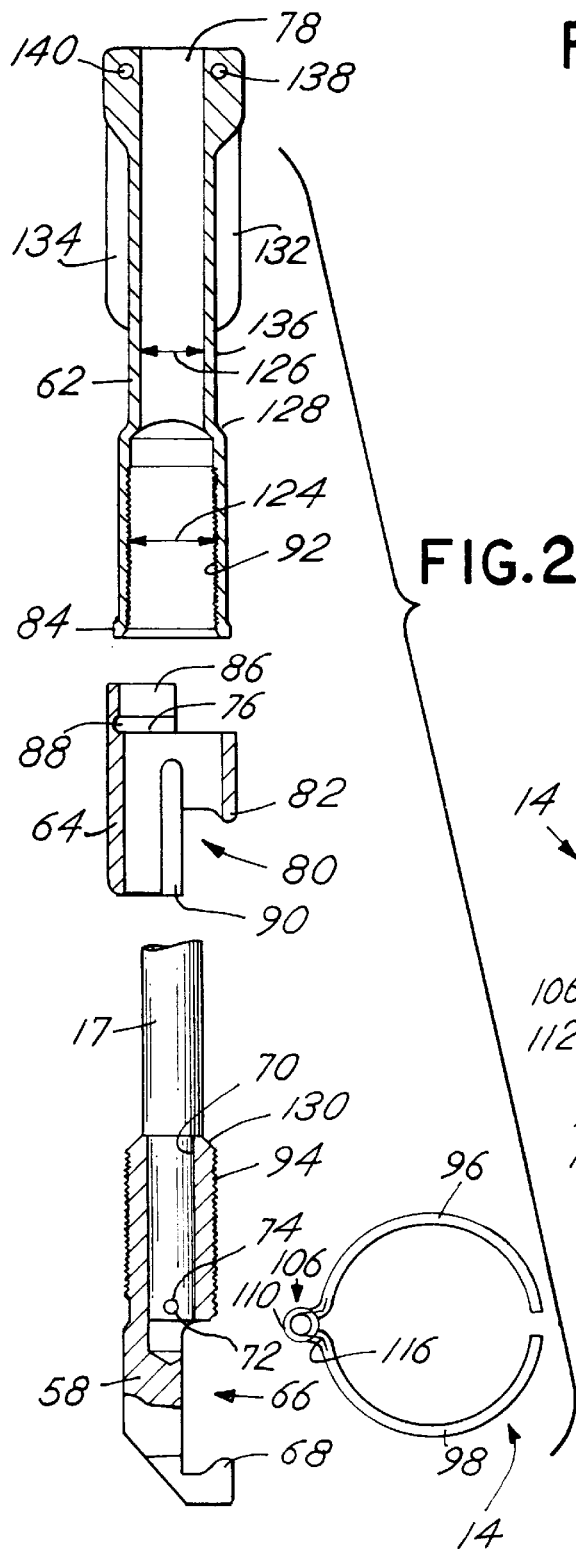
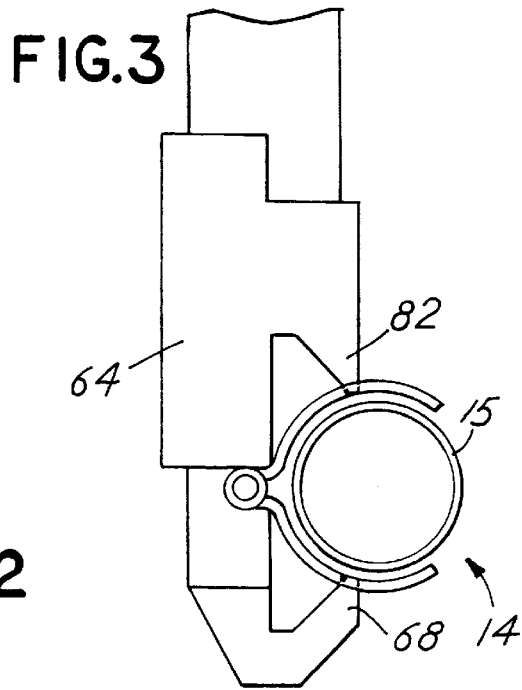
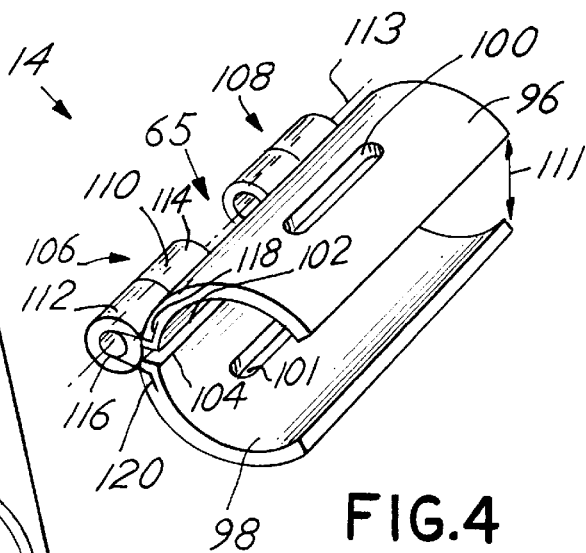

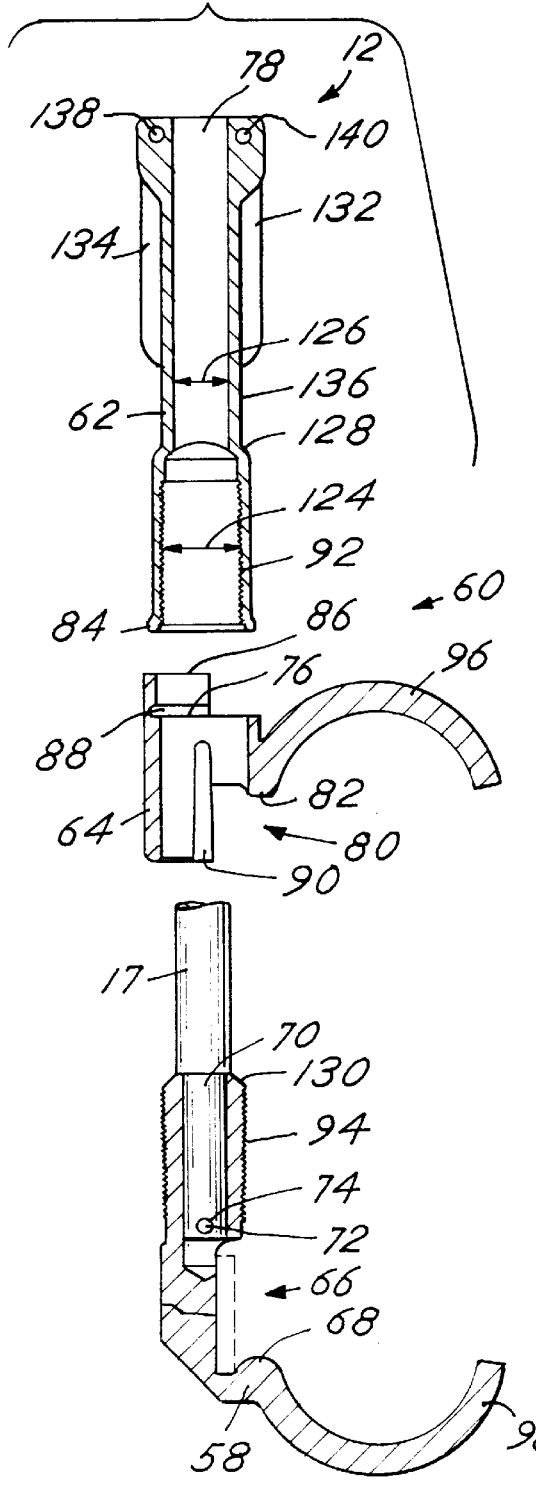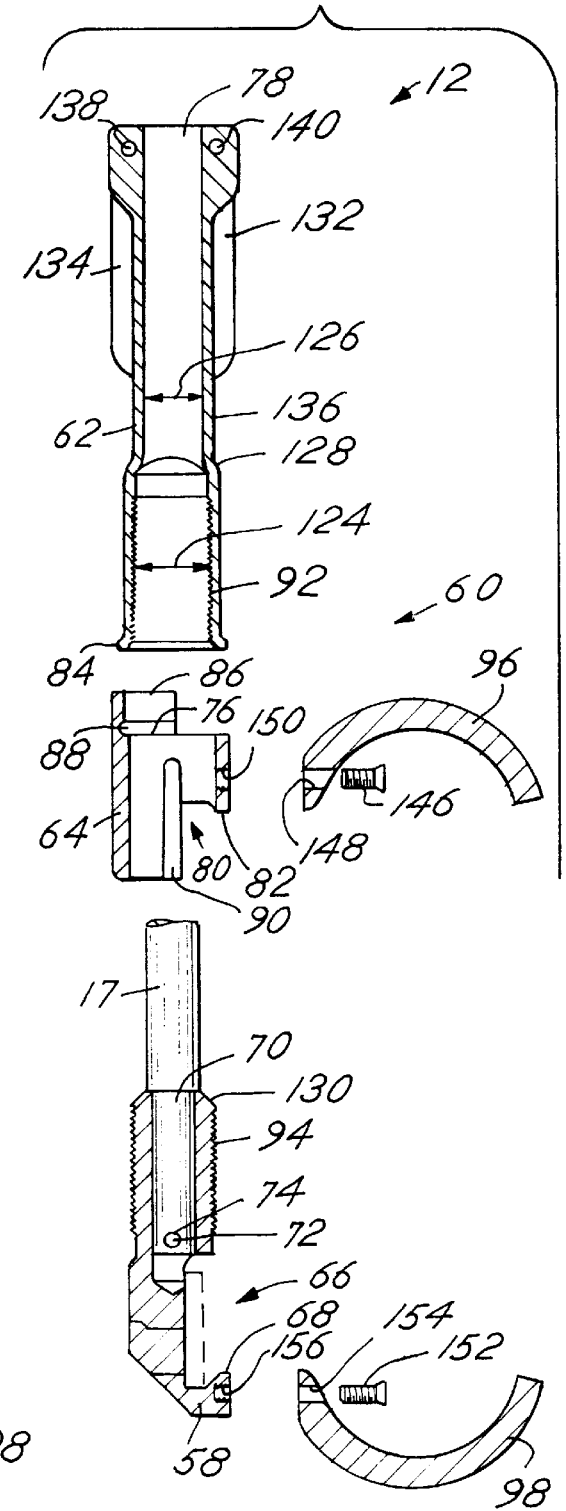

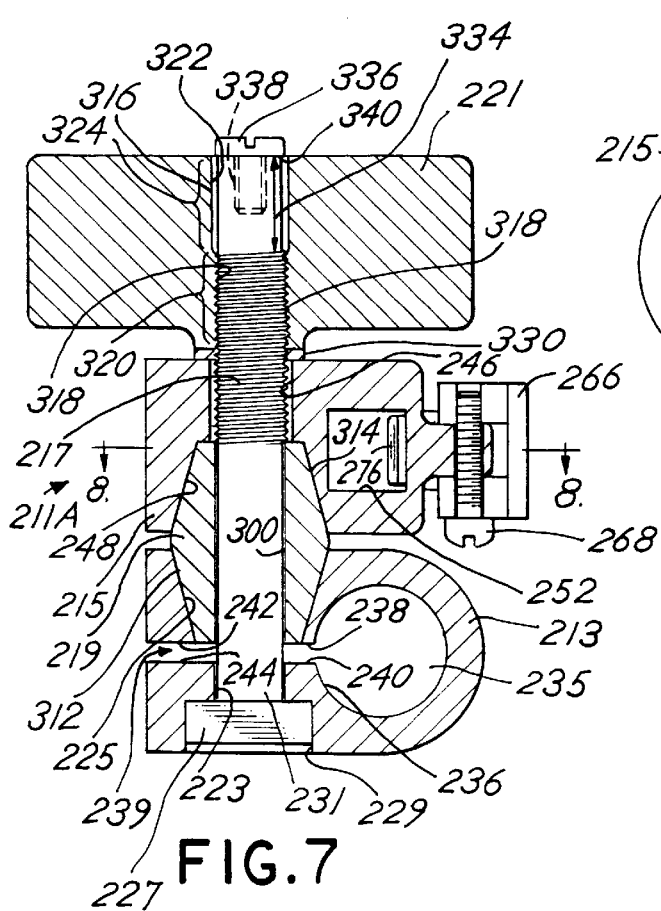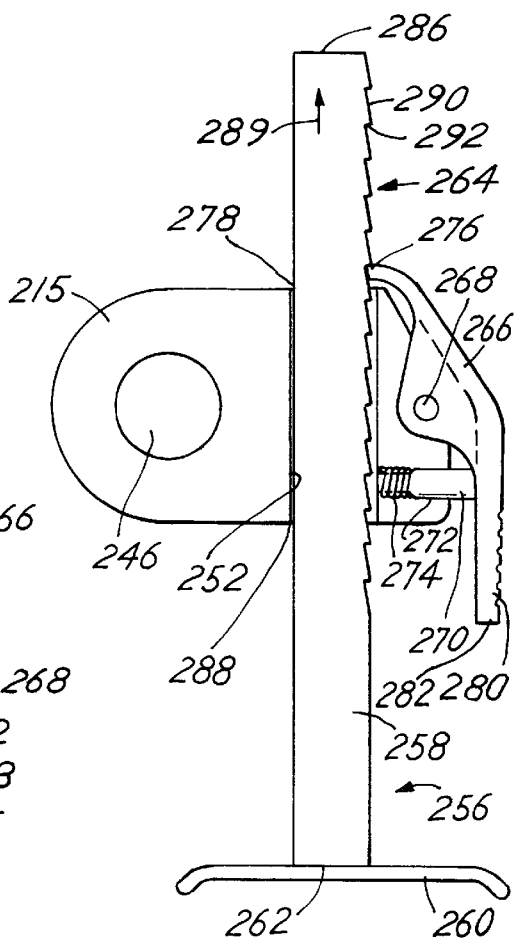
FIG.7
FIG.8

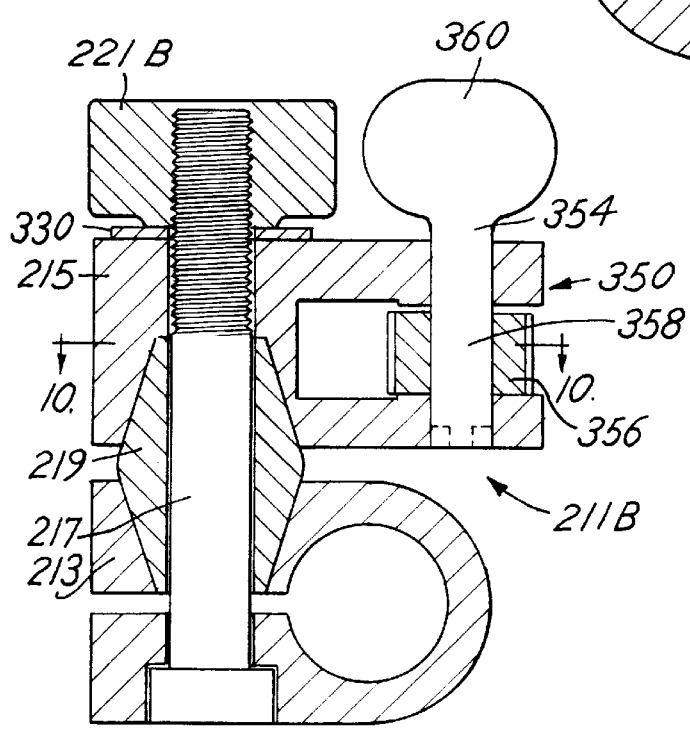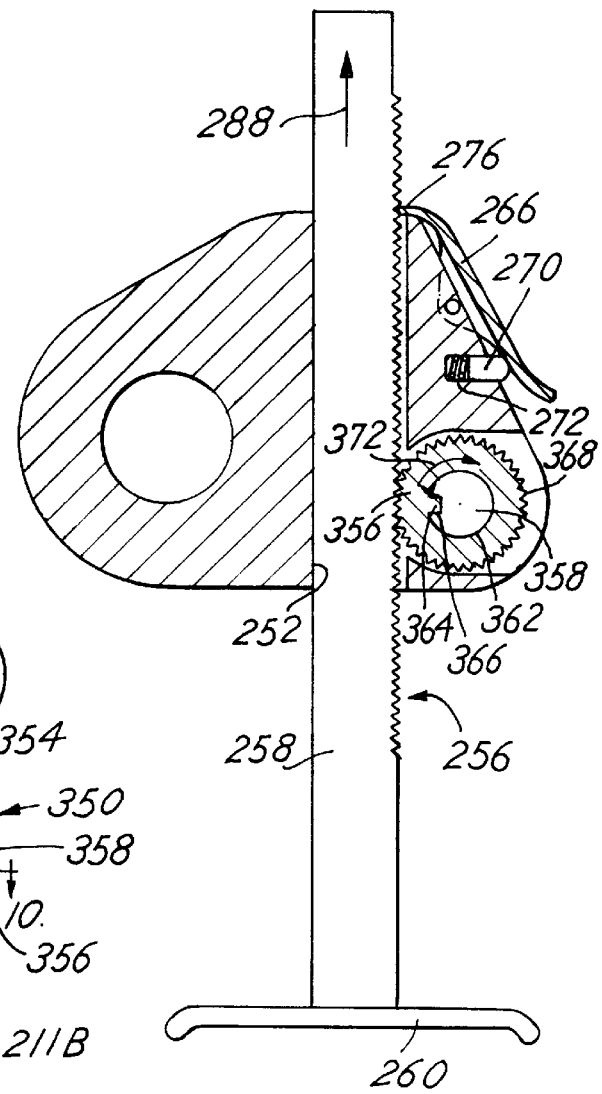

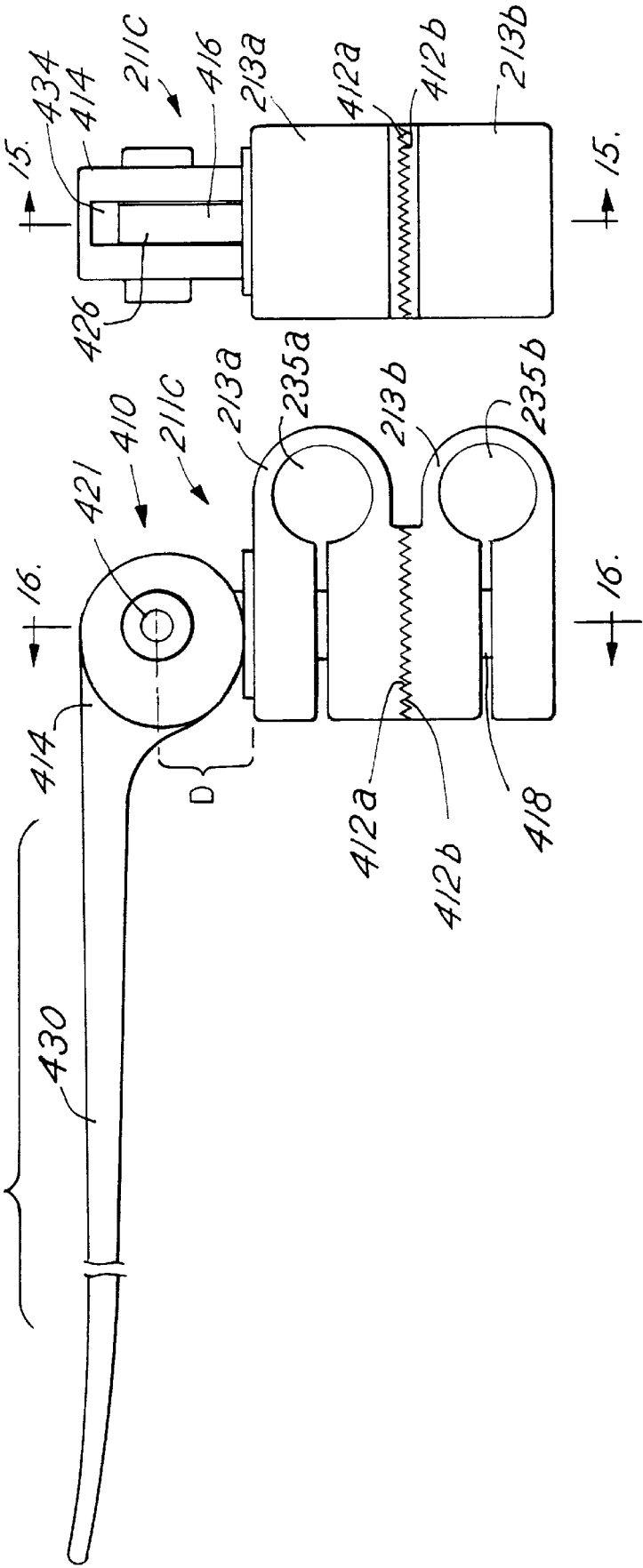

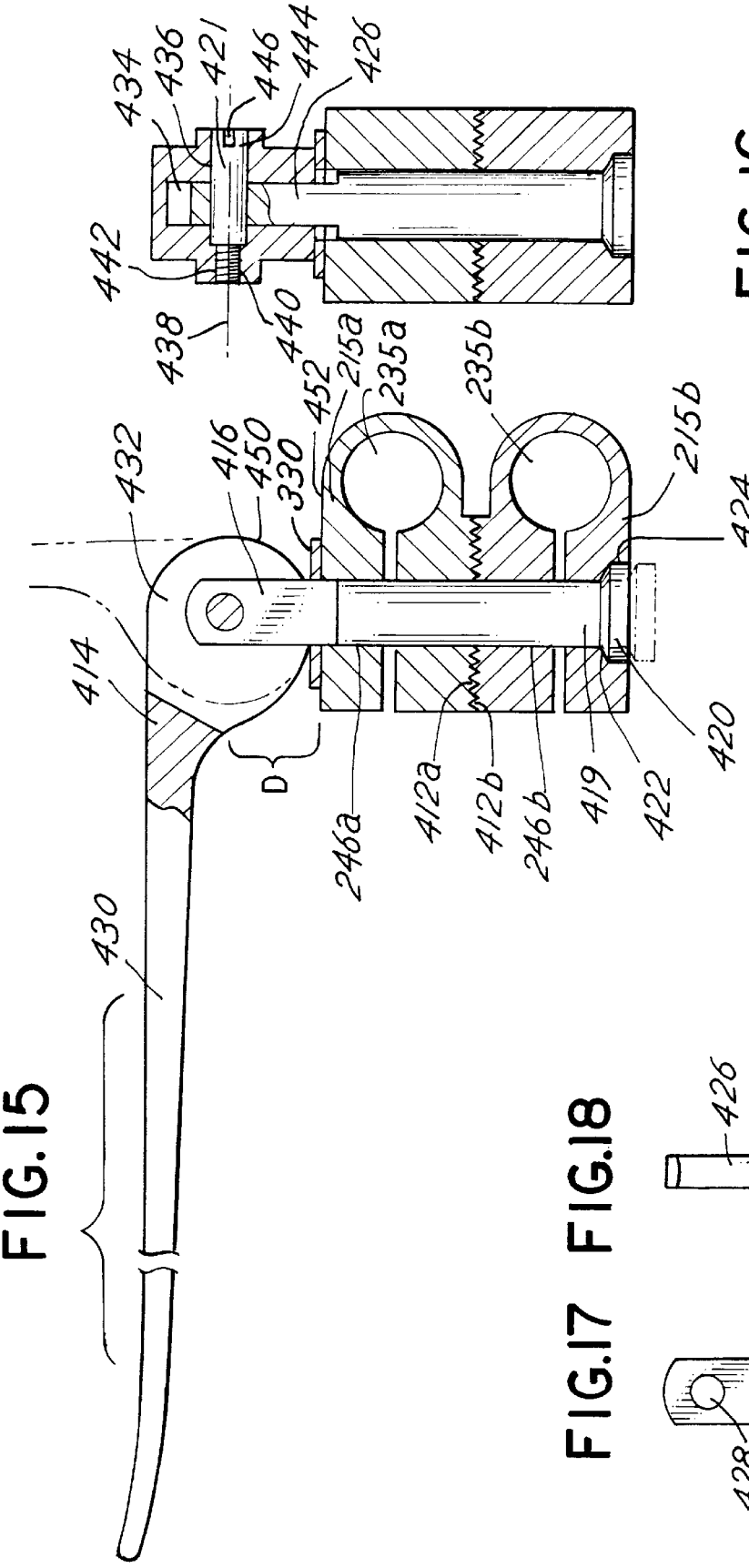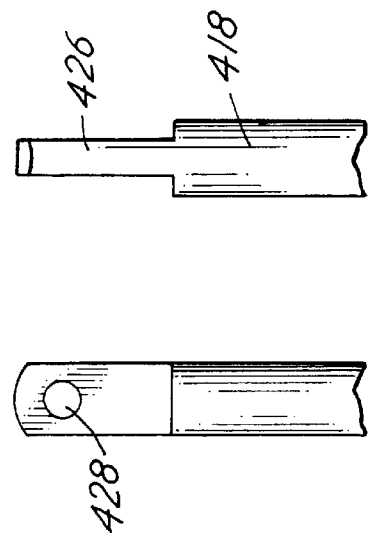

CAM TIGHTENED UNIVERSAL JOINT CLAMP

BACKGROUND OF THE INVENTION

This is a continuation of U.S. Ser. No. 08/482,023, filed Jun. 7, 1995 which is a continuation-in-part of U.S. Ser. No. 08/213,848 filed Mar. 15, 1994 now abandoned.

The invention relates to surgical apparatus for retracting anatomy to provide exposure of the operative site, and, more particularly, to a retraction apparatus which is sturdy, adjustable, conducive to thorough sterilization, and suited for use in conjunction with a tubular framed stretcher.

Retraction apparatus are used during surgical operations to access internal organs and bone structures. Variance in the types of surgery and patient size necessitates a device which is both adjustable and sturdy. Furthermore, the nature of a patient's injuries or the patient's condition may make it desirable to leave the patient on a tubular-framed stretcher during surgery as opposed to transferring the patient to a conventional operating table. In addition, equipment sterilization requirements call for a device which can be thoroughly cleansed by conventional means in a safe and easy manner.

Existing table mounted surgical retraction devices utilize rail clamps. A first type of rail clamp commonly used cannot be secured to an operating table without breaking the sterile field. Repositioning of this rail clamp during surgery must be performed by a non-sterile circulating nurse, thereby increasing the duration of the surgery. An example of such a rail clamp is disclosed in U.S. Pat. No. 4,617,916.

A second type of rail clamp can be secured to an operating table without breaking the sterile field. However, without disassembly, such rail clamps do not permit access to internal threads of the clamp for proper cleaning and lubrication. Saline solution and blood which is not completely removed during the sterilization process can subject the threads to premature galling, marring, and stripping. An example of such a rail clamp is disclosed in U.S. Pat. No. 4,254,763.

A third type of rail clamp can be secured to the rail of an operating table without breaking the sterile field and permits access to internal threads of the clamp for proper cleaning and sterilization without disassembly. However, this type of rail clamp cannot be secured to the frame of a conventional framed stretcher and, therefore, cannot be used in situations where the patient must remain on a framed stretcher during the surgical procedure. An example of such a rail clamp is disclosed in U.S. Pat. No. 4,971,038.

In addition, surgical retraction devices utilize universal connecting joint mechanisms. Such joint mechanisms consists of several parts which allow the surgeon to swivel and/or rotate the retractor blades into place. Examples of such devices are disclosed in U.S. Pat. Nos. 3,221,743, 4,617,916, and 5,025,780. However, moving such retractor blades requires loosening the universal joint, then moving the retractor blade and then retightening the joint. It would be highly desirable to have a universal joint mechanism which permits ease of movement of the retractor blade and the other joint components.

It is therefore an object of the present invention to provide an improved surgical retractor.

It is a further object of the present invention to provide a surgical retraction system having a rail clamp which can be secured to the frame of a conventional framed stretcher without breaking the sterile field and facilitates the cleaning, lubrication, and sterilization of internal threads without disassembling the clamp.

It is a further object of the present invention to provide a retraction system having a rail clamp which can be secured to either a conventional framed stretcher or to a conventional operating room table.

It is yet another object of the present invention to provide a retraction system having a universal connecting joint mechanism that is easy to use and permits quick release and repositioning of attachments such as retractors.

Still another object of the present invention is to provide a retraction system having a universal connecting joint mechanism which can be cleaned, sterilized and lubricated without being disassembled.

SUMMARY OF THE INVENTION

These and other objects of the invention are achieved in a surgical retraction system which retracts anatomy during all types of surgery. The retraction system includes a clamp which can be adjusted in order to fasten the overall retraction system anywhere along the frame of a framed stretcher, or a standard operating room table, without breaking the sterile field. In one embodiment, the jaws of the clamp comprise integral arcuate plates for seating against the frame of the stretcher. In an alternate embodiment, the jaws of the clamp are designed to seat against the rail of a conventional operating table and are able to clamp onto the stretcher frame through the use of an adapter. In either embodiment, the clamp facilitates exposure for cleaning, lubrication, and sterilization purposes.

The retraction system also includes extension arms which lend support to retractor blades extending downwardly into the operative site. The extension arms are supported by a post which, in turn, is supported by the clamp. When the clamp is secured to the stretcher frame, the retraction system is held firmly in place. The stability of the retraction system can be increased further by employing additional clamps and posts to support the extension arms.

In addition, the device includes extension arms which lend support to retractor blades extending downwardly into the operative site. A joint mechanism is used to connect the retractor blades to the extension arms. In one embodiment, the joint mechanism includes a ratchet member permitting quick adjustment of the retractor blades relative to the extension arms. In another embodiment, the joint mechanism includes a manual crank mechanism permitting greater leverage to be exerted on the retractor blade during retraction. It yet another embodiment, the joint mechanism includes a locking mechanism for permitting quick adjustment of the joint clamp components relative to each other.

BRIEF DESCRIPTION OF THE DRAWINGS

For a more complete understanding of this invention reference should now be had to the embodiment illustrated in greater detail in the accompanying drawings and described below by way of example of the invention.

In the drawings:

FIG. 1 is a perspective view of a surgical retraction system embodiment of the present invention;

FIG. 2 is an exploded cross-sectional side view of a single clamp, support post, and adapter of the retraction system of FIG. 1;

FIG. 3 is a partial side schematic view of a single clamp and adapter of the retraction system of FIG. 1;

FIG. 4 is a perspective view of the adapter of FIG. 3;

FIG. 5 is an exploded cross-sectional view of an alternate embodiment of a clamp for use in the retraction system of FIG. 1;

FIG. 6 is a cross-sectional side view of a an alternate embodiment of a clamp for use in the retraction system of FIG. 1;

FIG. 7 is a cross-sectional side view of a first embodiment of a joint clamp for use in the retraction system of FIG. 1;

FIG. 8 is a cross-sectional top view of FIG. 7 along line 8—8;

FIG. 9 is a cross-sectional side view of a second embodiment of a joint clamp for use in the retraction system of FIG. 1;

FIG. 10 is a cross-sectional top view of FIG. 9 along line 10—10;

FIG. 13 is a side view of a third embodiment of a joint clamp for use in the retraction system of FIG. 1;

FIG. 14 is an end view of the joint clamp of FIG. 13;

FIG. 15 is a cross-sectional side view of FIG. 14 along line 15—15;

FIG. 16 is a cross-sectional end view of FIG. 13 along line 16—16;

FIG. 17 is a partial front view of a shaft used in the third and fourth embodiments of the joint clamp;

FIG. 18 is a partial side view of a shaft used in the third and fourth embodiments of the joint clamp.

DETAILED DESCRIPTION OF A PREFERRED EMBODIMENT

Figure 11:
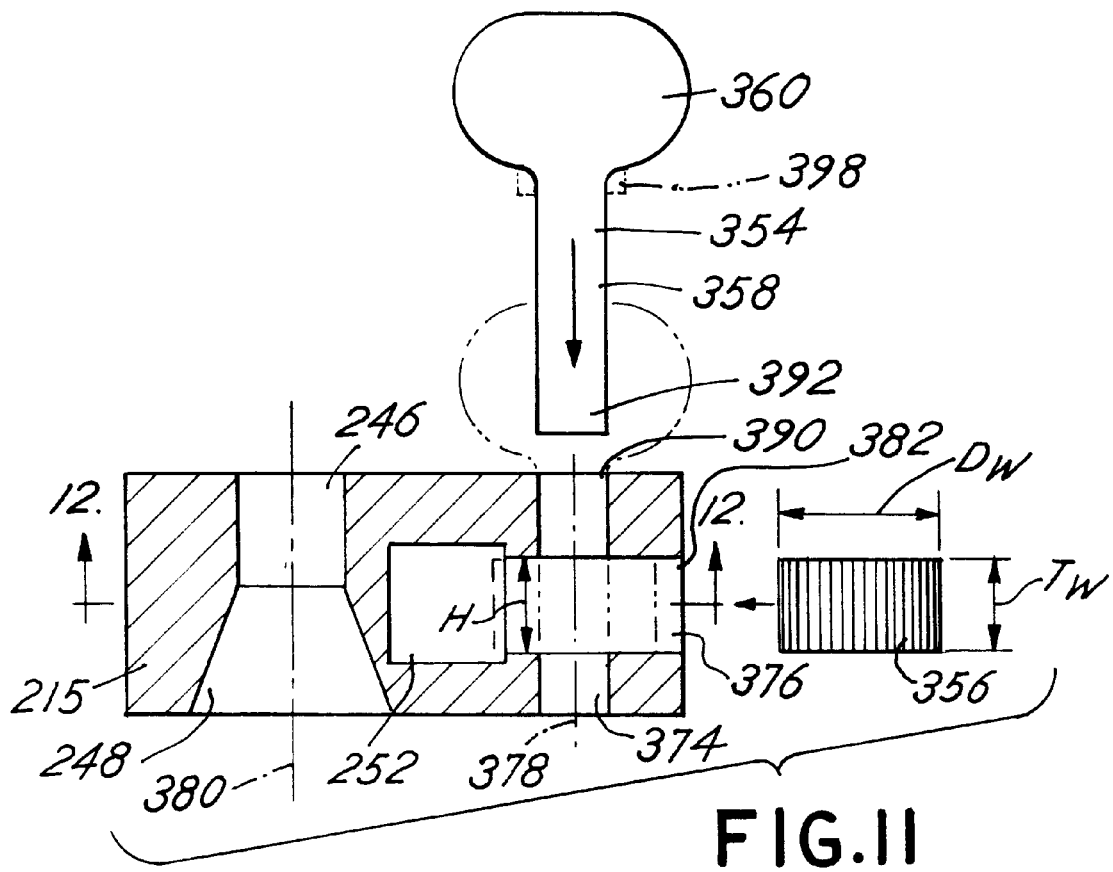
FIG. 11 is an exploded cross-sectional side view of FIG. 9 along line 11—11.

In the following detailed description, spatially orienting terms are used such as "left," "right," "vertical," "horizontal," and the like. It is to be understood that these terms are used for convenience of description of the preferred embodiments by reference to the drawings. These terms do not necessarily describe the absolute location in space, such as left, right, upward, downward, etc., that any part must assume.

As shown in FIG. 1, a surgical retraction system 10 includes an adjustable clamp 12 which is securable, through the use of an adapter 14, to the frame 15 of a conventional framed stretcher 16. A second adjustable clamp 12a is secured to the opposite frame 15a. A post 17 extends vertically from clamp 12 to provide support for a cross bar 18 which in turn provides support for a pair of extension arms 19, 20. Cross bar 18 is secured to post 17 by a multi-directional joint clamp 21. Extension arms 19, 20 are respectively secured to cross bar 18 by a pair of multi-directional joint clamps 22, 24. Additional joint clamps 26, 28 are disposed along extension arms 19, 20 for rigidly securing any number of retractor blades 34, 36 to extension arms 19, 20. As will suggest itself, extension arm 19 can also be secured directly to post 17 by a joint clamp.

Each retractor blade 34, 36 includes a blade portion 42 and a retractor arm 44. Blade portion 42 extends downwardly into the incision 46 made by the surgeon. Blade portion 42 is used to retract anatomy to make the incision 46 accessible to the surgeon.

As is shown in FIG. 2, clamp 12 includes a lower jaw 58 and an upper jaw 60. Upper jaw 60 includes two separable components: a jaw drive member 62 and an upper jaw carrying member 64. The three jaw components 60, 62, 64 are associated with post 17 such that post 17 can be secured rigidly to frame 15.

Lower jaw 58 is generally rectangular in shape and it includes an area 66 against which adapter 14 rests. A lip 68 protrudes outwardly and upwardly from lower jaw 58 for engaging adapter 14.

As can best be seen in FIG. 4, an open area 65 is located at the back of adapter 14 between two hinges 106, 108. Open area 65 provides a space for receiving lower jaw 58 and permitting adapter 14 to abut against area 66 of lower jaw 58. (See FIGS. 1 and 2.) Area 66 may be depressed or cut away, if necessary, for receiving adapter 14 so as to permit adapter 14 to open and close, as described below.

Referring again to FIG. 2, lower jaw 58 is axially bored in its upper end to form a cylindrical bore 70 which receives the lower end of post 17. A dowel pin 72 inserted through lower jaw 58 and through an aperture 74 in the lower end of post 17. Dowel pin 72 fastens post 17 to lower jaw 58 and prevents lower jaw 58 from being removed from the lower end of post 17. Post 17 extends upwardly through a hollow area 76 and a cylindrical bore 78 formed in upper jaw carrying member 64 and in jaw drive member 62, respectively.

Upper jaw carrying member 64 is generally rectangular in shape, having hollow area 76 disposed along its longitudinal axis. Upper jaw carrying member 64 has an upper cut away area 80 for receiving adapter 14. An upper lip 82 protrudes outwardly and downwardly from upper jaw carrying member 64 for engaging adapter 14.

Jaw drive member 62 is rotatable mounted to upper jaw carrying member 64 by an annular flange 84 formed at the lower end of jaw drive member 62. The upper end of upper jaw carrying member 64 includes a semicircular bored section 86 having a groove 88 sized to receive annular flange 84. During assembly, annular flange 84 is laterally moved into groove 88, and thereafter post 17 is passed through the hollow area 76 and cylindrical bore 78. Post 17 prevents jaw drive member 62 and upper jaw carrying member 64 from being detached. This structure prevents vertical separation of upper jaw carrying member 64 from jaw drive member 62 while permitting rotation of jaw drive member 62 relative to upper jaw carrying member 64. A vertical guide slot 90 is formed in both sides of upper jaw carrying member 64. Guide slot 90 is keyed to dowel pin 72 which protrudes from the sides of the lower jaw 58. As upper jaw carrying member 64 is driven downwardly to engage the top of adapter 14, dowel pin 72 moves upwardly within guide slot 90. This prevents rotational movement of the upper jaw carrying member 64 as jaw drive member 62 is rotated.

Jaw drive member 62 includes a set of internal threads 92 formed within cylindrical bore 78. A reciprocal set of threads 94 surrounds the upper portion of the lower jaw 58. The sets of threads 92, 94 engage each other as jaw drive member 62 is manually rotated in a clockwise direction. Referring additionally to FIG. 3, rotation of jaw drive member 62 drives upper jaw carrying member 64 downwardly, forcing lower lip 68 and upper lip 82 toward one another to engage adapter 14. Jaw drive member 62 is rotated until adapter 14 is securely compressed against stretcher frame 15.

As is shown in FIG. 4, adapter 14 includes a first arcuate plate 96 and a second arcuate plate 98. Plates 96, 98 are sections of a cylinder having a radius of curvature which corresponds to the radius of tubular frame 15, such that when adapter 14 engages frame 15 the area of contact is maximized. The inside surfaces of plates 96, 98 form jaw surfaces and may be roughened or may carry teeth or an abrasive surface, etc.

First arcuate plate 96 has a slot 100 which defines a first engaging structure. Similarly, second arcuate plate 98 has a slot 101 which defines a second engaging structure. Slots 100, 101 are surface features or surface components which provide a structure which is mateable with jaw lips 68, 82. Surface features other than slots 100, 101 may be utilized including depressions or projections formed in the outer surface of arcuate plates 96, 98.

First and second arcuate plates 96, 98 are pivotally connected at their respective medial distal edges 102, 104 by means of first and second hinges 106, 108. First hinge 106 includes a first cylindrical shell 110 attached to first arcuate plate 96, a second cylindrical shell 112 attached to second arcuate plate 98, and a hinge pin 114 passing through the first and second cylindrical shells 110, 112 along their common axis 113. A spring 116 is mounted on hinge 106 with its first end 118 attached to the first arcuate plate 96 and its second end 120 attached to the second arcuate plate 98 such that the adapter 14 is urged into an open position. Second hinge 108 is constructed similarly to first hinge 106 and, hence, it will not be explained in greater detail.

When adapter 14 is in its open position, the distance 111 (See FIG. 4) between the proximal edges of plates 96, 98 is sufficient to permit adapter 14 to slip laterally over cylindrical stretcher frame 15. In its open position, adapter 14 does not grip stretcher frame 15. Adapter 14 is shown in FIGS. 1, 3 and 4 in a closed position in which it grips frame 15 preventing movement of adapter 14 relative to frame 15.

When jaw drive member 62 is manually rotated in a counterclockwise direction, upper jaw 60 recedes from lower jaw 58. As upper jaw recedes 60, spring 116 (See FIG. 4) urges the adapter 14 into its open position. Advantageously, the engagement of slot 100 with upper lip 82 and the engagement of slot 101 with lower lip 68 is maintained when adapter 14 is in its open position. As upper jaw 60 recedes from lower jaw 58, adapter 14 relinquishes its grasp on frame 15. Once adapter 14 reaches its open position, the adapter and jaw combination are held together by the bias of spring 116 and may be laterally removed from frame 15.

Continued counterclockwise rotation of jaw drive member 62 causes complete separation of thread sets 92, 94. After thread sets 92, 94 separate from each other, upper jaw 60 freely slides along post 17 and adapter 14 is disengageable from clamp 12. Once clamp 12 is disengaged from adapter 14, clamp 12 may be used to grip the rail (not shown) of a conventional operating room table without adapter 14 in place.

With upper jaw 60 disengaged from lower jaw 58, thread sets 92, 94 become exposed for cleaning. The inner threaded diameter 124 of internal threads 92 is larger than the diameter of support posts 17, thereby permitting ultrasonic cleaning and auto claving to easily reach internal threads 92. In this position, thread set 94 is also openly exposed for cleaning and auto claving.

The inner diameter 124 of thread set 92 is also larger than the diameter 126 of upper portion of hollow area 78 above thread set 92. A bottleneck (See FIG. 2) at location 128 contacts an angled periphery surface 130 of lower jaw 58 to control the extent of opposing movement of jaws 58, 60. Retaining pin 122 (FIG. 1) and dowel pin 72 serve as a pair of stops which maintain the components as a single unit structure. The structure, thus, does not need to be dissembled into several components in order to be cleaned, and can be easily manipulated to perform its clamping function.

A pair of manual control handles 132, 134 are pivotally fastened at the upper most end of jaw drive member 62 by respective pivot pins 138, 140. The mid section 136 of jaw drive member 62 is elongated a sufficient length to extend handles 132, 134 above the field of sterilization, i.e., generally above waist height in the operating room. This permits the surgeon to operate clamp 12 via handles 132, 134 without breaking the field of sterilization. Furthermore, since spring 116 maintains the engagement of adapter 14 to jaws 58, 62, the surgeon can remove and resecure the adapter 14-clamp 12 combination as many times as is necessary during a surgical procedure without breaking the field of sterilization.

FIGS. 5 and 6 show alternate embodiments of clamp 12. In FIG. 5, adapter 14 is integrally formed with upper and lower jaws 60, 58. More specifically, first arcuate plate 96 is integrally formed with upper jaw carrying member 64, and second arcuate plate 98 is integrally formed with lower jaw 58. In FIG. 6, first arcuate plate 96 and second arcuate plate 98 are detachably mounted (releasably engaged) to upper jaw carrying member 64 and lower jaw 58, respectively. This embodiment permits clamp 12 to be disengaged from plates 96, 98 so that clamp 12 can be used with a rail of a conventional operating room table. As can be seen in FIG. 6, plate 96 is secured to jaw carrying member 64 by a threaded fastener 146 which passes through a bore 148 in plate 96 and engages reciprocal threads 150 in jaw carrying member 64. Similarly, plate 98 is secured to lower jaw 58 by a threaded fastener 152 which passes through a bore 154 in plate 98 and engages reciprocal threads 156 in lower jaw 58. Other methods can be used to releasably connect the plates 96, 98 to jaw members 64, 58 without departing from the scope of the invention. For example, plates 96, 98 may be constructed with dove tail projections (not shown) which slidably engage reciprocal dove tail grooves (not shown) in jaw members 64, 58, respectively. A latch or stop member can also be provided to control the position or securement of plates 96, 98 in jaw members 64, 58.

Referring now to FIGS. 7 and 8, a first embodiment of a universal joint clamp 211A is shown in detail. Joint clamp 211A can take the position of any one of the single joint clamps 21, 22, 23, 24, 26, 28 shown in FIG. 1. Reference is made in connection to clamp 211 to U.S. Pat. No. 5,025,780, of the same inventor, which is incorporated herein by reference. Joint clamp 211A is formed from a jaw or clamping member 213, a ratchet member 215, a partially threaded cylindrical axle or shaft 217, a wedge member 219, and a securing knob 221. Knob 221 is manually rotated in order to lock clamping member 213 and ratchet member 215 relative to shaft 217, as well as to cause a gripping action to take place by clamping member 213.

Clamping member 213 includes a cylindrical bore 223 for receiving shaft 217 and a conical bore 225 for receiving wedge member 219. Shaft 217 is cylindrical in cross section and it has an integral square head 227. A square opening 229 formed in the bottom of clamping member 213 receives head 227 for fixing shaft 217 within bore 223. Head 227 prevents clamping member 213 from being removed from the distal end 231 of shaft 217. As will suggest itself, head 227 and opening 229 can take other shapes. For example, both may have a hexagonal geometry. Shaft 217 may also be secured to clamping member 213 by other means such as welding, riveting, etc.

Clamping member 213 further includes a cylindrical passage 235 which is defined by a broken cylindrical surface 236. Cylindrical surface 236 is broken along two parallel line edges 238, 240 which run the axial length of the surface 236 to define a gap 239. Line edges 238, 240 are movable with respect to one another in order to shorten the gap 239 and thus constrict the area circumscribed by cylindrical surface 236. Each line edge 238, 240 defines a respective planar surface 242, 244. Each planar surface 242, 244 is parallel to the longitudinal axis of cylindrical passage 235. The application of a force against conical bore 225 by wedge member 219 in a direction parallel to the longitudinal axis of shaft 217 serves to move planar surfaces 242, 244 toward each other constricting the area within cylindrical passage 235.

Rachet member 215 includes a cylindrical bore 246 for receiving shaft 217 and a conical bore 248 for receiving wedge member 219. Rachet member 215 is positioned on shaft 217 between knob 221 and wedge member 219. Rachet member 215 also includes a transverse bore 252 having an axis which is perpendicular to the axis of cylindrical bore 246. Transverse bore 252 is adapted to receive a retractor arm 258 (FIG. 8) of a retractor blade 256.

As shown in FIG. 8, retractor blade 256 includes retractor arm 258 and a blade portion 260 mounted at a distal end 262 of retractor arm 258. In the illustrated embodiment, retractor arm 258 and traverse bore 252 have square cross sections; however, transverse bore 252 and retractor arm 258 may have other cross sections, such as cylindrical cross sections.

A plurality of rachet teeth 264 are spaced along one surface of retractor arm 258 at regular intervals. Rachet member 258 includes a quick-release rachet arm 266 for releasably engaging rachet teeth 264 to lock the position of retractor arm 258 within transverse bore 252. Rachet arm 266 is pivotally connected to rachet member 215 by a fastener 268 such as a bolt or a pivot pin. A pin 270 is disposed in a bore 272 which is formed in the side of the rachet member 215. Pin 270 is biased outwardly against rachet arm 266 by a spring 274 located at the bottom of bore 272. Pin 270 biases rachet arm 266 to a first position at which a first end 276 of rachet arm 266 extends across a first end 278 of transverse bore 252. At its first position, the first end 276 of rachet arm 266 engages rachet teeth 264 when retractor arm 258 is positioned in transverse bore 252. A handle 280 is provided at the second end 282 of rachet arm 266 for pivoting rachet arm 266 to a second position at which the first end 276 of rachet arm 266 disengages rachet teeth 264. When ratchet arm 266 is at its second position, retractor arm 258 freely slides within transverse bore 252 in both directions.

During surgery, the proximate end 286 of retractor arm 258 is inserted into the second end 288 of transverse bore 252 with rachet teeth 264 facing rachet arm 266, as is shown in FIG. 8. The first end 276 of rachet arm 266 mates with rachet teeth 264 to lock retractor blade 256 in a fixed position within transverse bore 252. Advantageously, rachet teeth 264 are spaced to permit small incremental adjustments of retractor blade 256 with respect to rachet member 215. Rachet teeth 264 are configured such that retractor arm 258 can be pulled through transverse bore 252 in the direction indicated by the arrow 289, i.e. in a direction which draws blade portion 260 closer to rachet member 215.

For this purpose, each tooth 264 includes an angled surface 290 disposed at an angle to the direction 289 and a flat surface 292 disposed perpendicular to the direction 289. Angled surfaces 290 automatically biases and pivots rachet arm 266 towards its second position as retractor arm 258 moves through transverse bore 252 in the direction 289. By contrast, the flat surfaces 292 of rachet teeth 264 extend generally perpendicular to the edge of retractor arm 258 to prevent retractor arm 258 from being moved in a direction opposite to that of direction 288 unless rachet arm 266 is pivoted to its second position using handle 280.

Referring again to FIG. 7, wedge member 219 includes a cylindrical bore 300 for receiving shaft 217. Wedge member 219 is relatively loosely mounted on shaft 217 between rachet member 215 and clamping member 213. Wedge member 219 includes opposing exterior conical surfaces 312, 314 which are adapted to seat in the conical bores 225, 248 of clamping member 213 and rachet member 215, respectively. As will suggest itself, wedge member 219 can be replaced by forming a conical extending outer surface on either clamping member 213 or rachet member 215 and a reciprocal conical bore in the other member 213, 215. Alternatively, wedge member 219 can be replaced by sets of reciprocal locking teeth formed on the bottom of rachet member 215 and the top of clamp member 213, as shown in FIG. 13.

Knob 221 includes a cylindrical bore 316 for receiving shaft 217. Bore 316 includes a set of threads 318 formed along a bore section 320 and a smooth cylindrical surface 322 formed along the remaining bore section 324. Smooth surface 322 is generally larger in diameter than the inner diameter of threads 318. Threads 318 mate with a reciprocal set of threads 328 formed on shaft 217.

As knob 221 is rotated in a clockwise direction, threads 318, 328 guide knob 221 along shaft 217 and towards rachet member 215. A spacing washer 330 centered about shaft 217 between knob 221 and rachet member 215 prevents contact therebetween. Clockwise rotation of knob 221 pushes rachet member 215 and wedge member 219 towards clamping member 213 until wedge member 219 seats in the conical bores 225, 248, of members 213, 215.

Once wedge 219 becomes seated in clamping member 213 and rachet member 215, further clockwise rotation of knob 221 forces planar surfaces 242, 244 together and causes cylindrical passage 235 to constrict. When cylindrical passage 235 is at its expanded position, it is of size sufficient for receiving extension arms 19, 20, post 17 or cross bar 18. Constriction of cylindrical passage 235 causes surface 236 to grip the cylindrical arm or arm (not shown) passing through cylindrical passage 235, thereby fixing the position of the arm relative to members 213, 215.

The threads 328 of shaft 217 are disposed in an area along shaft 217 which extends into bore 246 of rachet member 215 in order to provide sufficient movement of knob 217 for enabling constriction of cylindrical passage 235. As will suggest itself, the diameter and shape of cylindrical passage 235 can be varied so as to facilitate the joining of cylindrical objects of different diameters as well as noncylindrical objects.

Counter clockwise rotation of knob 221 moves knob 221 away from the members 213, 215, 219, causing clamping member 213 to relinquish its grasp on any object occupying cylindrical passage 235. With further counter clockwise rotation of knob 221, the two sets of threads 318, 328 will loose contact with one another, thereby allowing knob 221 to freely and rotatably slide along the unthreaded portion 334 of shaft 217. The length of the unthreaded portion 334 of the shaft enables the thread sets 318, 324 to be completely separated from one another.

Knob 221 is prevented from being completely removed from shaft 217 by a flathead screw 336 disposed in a threaded bore 338 in end of shaft 217. The inner diameter of the threads 318 on knob 221 prevents knob 221 from passing beyond the head 340 of flathead screw 336.

Flathead screw 336 and integral head 227 serve as a pair of stops which maintain the components 213, 215, 219, 221 as a single-unit structure. As a result, clamp 211 will not fall apart when knob 221 is loosened from the threaded portion of shaft 117, and, hence, clamp 211 does not require reassembly after cleaning. Rather, reassembly occurs by mere rotation of knob 221. As will suggest itself, means other than flathead screw 336 and integral head 227 can be used to provide stops for clamp 211A. Shaft 217 can also be axially lengthened to accommodate additional members similar to the members 213, 215.

Referring now to FIGS. 9–12, a second embodiment of a joint clamp 211B is shown in detail. Reference numerals previously designated in connection with FIGS. 7–8 are used to identify like components in FIGS. 9–12. The primary difference between the joint clamp 211A of the first embodiment and the joint clamp 211B of the second embodiment is that joint clamp 211B incorporates a crank mechanism 350 for moving retractor arm 258 within transverse bore 252. Joint clamp 211B also utilizes a low profile knob 221B to permit greater access to crank mechanism 350. Low profile knob 221B has a lower profile and a smaller diameter than the knob 221 used in the first embodiment. It will be appreciated that flathead screw 336 can be used to secure low profile knob 221B to the shaft 217, although it is not illustrated in FIG. 9.

Crank mechanism 350 includes a crank 354 and a toothed wheel 356 mounted for rotation relative to rachet member 215. Crank 354 has a cylindrical rod portion 358 which terminates in a handle 360. Toothed wheel 356 includes a center bore 362 for receiving rod portion 358. (See FIG. 10.) A means 363 connects toothed wheel 356 to rod portion 358 for rotation therewith. For example, a raised protuberance or a key 364 can be formed in center bore 362 for engaging a reciprocal groove or keyway 366 formed in rod portion 358.

A plurality of teeth 368 are spaced about the outer edge of toothed wheel 356 at regular intervals. Toothed wheel 356 is mounted in rachet member 215 such that its teeth 368 engage the rachet teeth 264 when retractor arm 258 is positioned in transverse bore 252. Rotation of crank 354 in the clockwise direction indicated by arrow 372 draws retractor arm 258 through transverse bore 252 in the direction of arrow 288. Rachet teeth 264 may include angled surfaces 290 and flat surfaces 292 as described above in connection with FIGS. 7–8.

Figure 12:
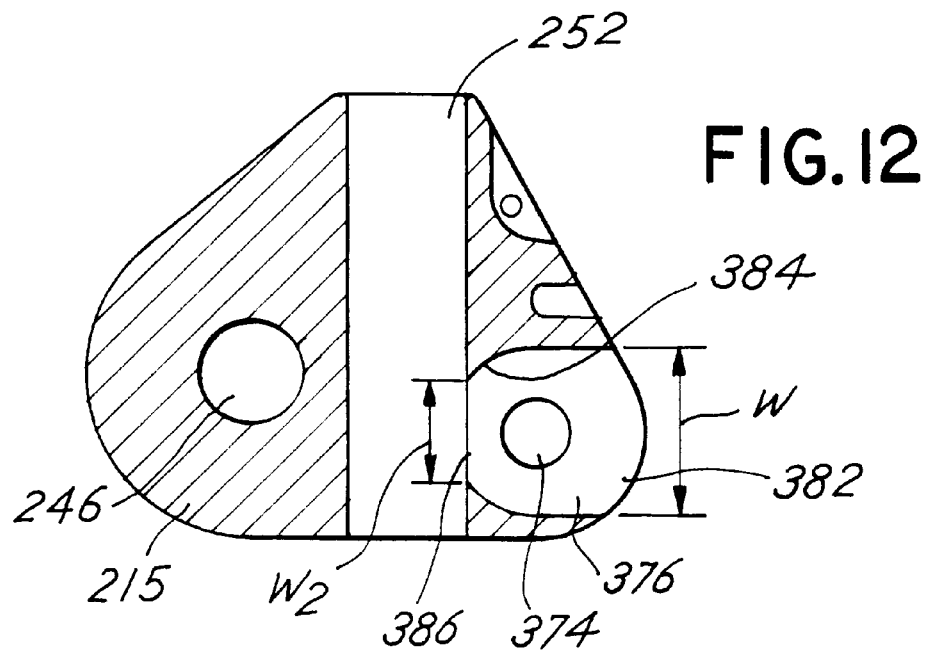
FIG. 12 is a cross-sectional top view of FIG. 11 along line 12—12.

As can best be seen in FIGS. 11 and 12, rachet member 215 has a second cylindrical bore 374 adapted to receive rod portion 358, and a second transverse bore 376 adapted to receive toothed wheel 356. Second cylindrical bore 374 extends completely through rachet portion 215 and has an axis 378 which is generally parallel to the axis 380 of cylindrical bore 246. Second transverse bore 376 has a width W which is slightly larger than the outer diameter $D_w$ of toothed wheel 356 and a height H which is slightly larger than the thickness $T_w$ of toothed wheel 356. Second transverse bore 376 intersects both second cylindrical bore 374 and transverse bore 252 and includes an outer opening 382 which permits toothed wheel 356 to be slid laterally into second transverse bore 376.

To assemble crank mechanism 350, toothed wheel 356 is slid laterally into second transverse bore 376 through outer opening 382. Second transverse bore 376 has an arced inner wall 384 terminating in a reduced width opening 386 which connects second transverse bore 376 to transverse bore 252. (See FIG. 12). Reduced width opening 386 has a width $W_2$ which is smaller than the outer diameter $D_w$ of toothed wheel 356 to prevent toothed wheel from sliding completely into-transverse bore 252. Arced inner wall 384 also aids in positioning the toothed wheel 356 in second transverse bore 376 during assembly. Once toothed wheel 356 is positioned in second transverse bore 376, rod portion 358 is slid into place through the top end 390 of second cylindrical bore 374. When crank 354 is in place, the bottom end 392 of rod portion 358 extends through the center bore 362 of toothed wheel 256 and into the bottom end 396 of second cylindrical bore 374 (See FIG. 9).

A limiting means can be provided for limiting the distance that rod portion 358 is inserted into second cylindrical bore 374. For example, rod portion 358 can include an increased diameter collet 398 positioned at its top end, adjacent handle 360, as is illustrated by phantom line in FIG. 11. Alternatively, a washer (not shown) can be positioned on rod portion 358 between the top of rachet member 215 and handle 360. As still another alternative, the bottom ends of second cylindrical bore 374 and rod portion 358 can have reduced diameters, as is illustrated by phantom line in FIG. 9.

Referring to FIGS. 13–19, third and fourth embodiments of joint clamp 211C, 211D are shown in detail. The joint clamps 211C, 211D both incorporate a quick release mechanism 410 which permits rapid adjustment and positioning of the joint clamp and its components. Reference numerals previously designated in connection with FIGS. 7–12 are used to identify like components in FIGS. 13–19.

Figure 20:
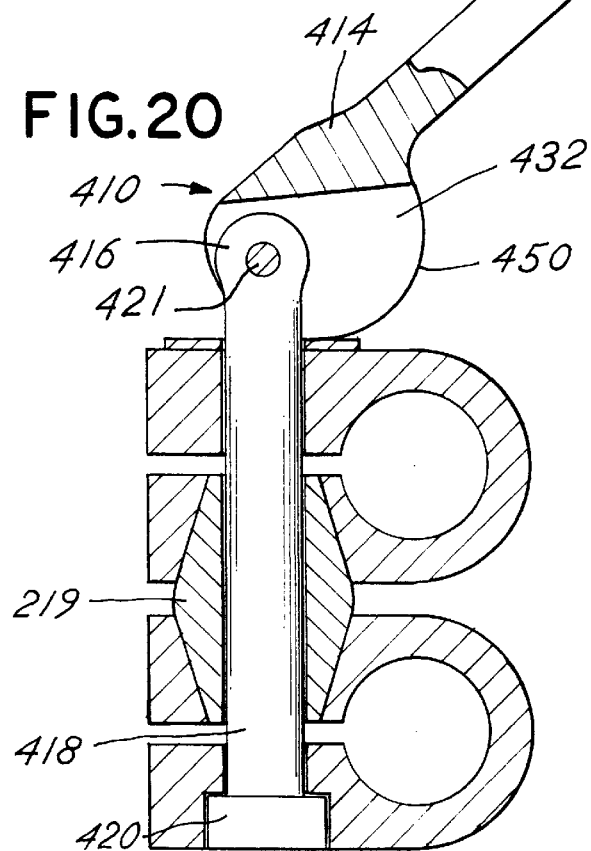
FIG. 20 is a cross-sectional side view of a fifth embodiment of a joint clamp for use in the surgical retractor system of FIG. 1.

Referring to FIGS. 13–18, the joint clamp 211C of the third embodiment uses quick release mechanism 410 in connection with first and second clamp members 213a, 213b. Joint clamp 211C also utilizes sets of locking teeth 412a, 412b instead of wedge member 219 to fix the position of the clamp members 213a, 213b relative to each other. A first set of locking teeth 412a is disposed on the bottom of first clamp member 213a and a second set of locking teeth 412b is disposed on the top of second clamp member 213b. The sets of locking teeth 412a, 412b engage each other when clamp members 213a, 213b are compressed together by quick release mechanism 410, thereby fixing the positions of clamp members 213a, 213b relative to one another. As will be appreciated, wedge member 219 can be used with quick release mechanism 410 instead of locking teeth 412a, 412b as shown in FIG. 20.

Quick release mechanism 410 includes a cam lever 414 pivotally connected about the top 416 of shaft 418 by a pivot pin 421. Shaft 418 may be cylindrical in cross section, and extends upwardly through the cylindrical bores 246*a*, 246*b* in clamp members 213*a*, 213*b*. (See FIGS. 15 and 16.) An integral head 420 formed at the bottom 419 of shaft 418 is generally round and it has a tapered top 422. An increased diameter counterbore 424 formed in the bottom of clamp member 215*b* is configured to receive integral head 420 when shaft 418 is positioned in the cylindrical bores 246*a*, 246*b*. As can best be seen in FIGS. 17–18, the top 416 of shaft 418 includes a flat portion 426. A bore 428 extending through the flat portion 426 of shaft 418 and is sized to pivotally engage pivot pin 421. (See FIG. 16.)

Cam lever 414 includes an elongated handle 430 which terminates in a cam portion 432. Cam portion 432 includes a center slot 434 sized to slidably receive the flat portion 426 of shaft 418. (See FIG. 16.) A transverse bore 436 formed in cam portion 432 along an axis 438 perpendicular to center slot 434 is sized to receive pivot pin 421. Pivot pin 421 is generally smooth and cylindrical, and has a threaded portion 440 at its distal end. Pivot pin 421 extends through bores 428, 436 to pivotally connect cam lever 414 to shaft 418. Reciprocal threads 442 formed in one end of transverse bore 436 threadably engage the threaded portion 440 of pivot pin 421 to secure pivot pin 421 to cam lever 414. The proximate end 444 of pivot pin 421 includes a slot 446 adapted to receive the head of a screwdriver to permit pivot pin 421 to be forcibly screwed into cam lever 414.

Cam lever 414 is pivotally movable about shaft 418 between a first or closed position illustrated with solid lines in FIG. 15 and a second or open position illustrated with phantom lines in FIG. 15. The outer edge 450 of cam portion 432 is eccentric, i.e. multiply curved, such that the distance D between the center of transverse bore 436 and the top 452 of clamp member 213*a* increases as cam lever is moved from its open position towards its closed position. Hence, movement of cam lever 414 towards its closed position draws shaft 418 upwardly through cylindrical bores 246, compressing clamp members 213*a*, 213*b* between the outer edge 450 of cam member 432 and the integral head 420 of shaft 418. Compression of clamp members 213*a*, 213*b* initially causes the sets locking teeth 412*a*, 412*b* to engage each other, thereby fixing the positions of the clamp members 213*a*, 213*b* relative to each other. Further compression of clamp members 213*a*, 213*b* constricts the area circumscribed by cylindrical passages 235*a*, 235*b* to secure clamping members to the arms (not shown) passing through cylindrical passages 235*a*, 235*b*. Self-lubrication washer 330 is disposed on shaft 418 between the top 452 of clamping member 213*a* and the outer edge 450 of cam member 432 to reduce galling of cam lever 432.

Because integral head 420 is rounded, as opposed to being square as in the first and second embodiments (FIGS. 7–10), shaft 418 can be rotated 360°, even when integral head 420 is partially drawn into counterbore 424. This permits the surgeon to rotate handle 430 to a convenient position, even after clamp members 213*a*, 213*b* have been partially compressed. As will suggest itself, a square head and square opening (see FIGS. 7–10) can be substituted for the round integral head 420 and counterbore 424 of FIGS. 13–19.

Rotation of cam lever 414 towards its open position moves shaft 418 downwardly through cylindrical bores 246*a*, 246*b*. When cam lever 414 is at its open position, integral head 420 extends beyond the bottom of clamp member 413*b*. At the open position, clamp members 213*a*, 213*b* are loosely held on shaft 418, and they can be rotated relative to one another about shaft 418. Integral head 420 prevents clamp members 213*a*, 213*b* from being removed for the bottom end 419 of shaft 418. The absence of compression on clamp members 213*a*, 213*b* expands cylindrical passages 235*a*, 235*b* to their greatest diameter, allowing clamp members 213*a*, 213*b* to be moved relative to arms (not shown) positioned in cylindrical passages 235*a*, 235*b*. The open position also allows the various clamp components to be accessed for cleaning.

Figure 19:
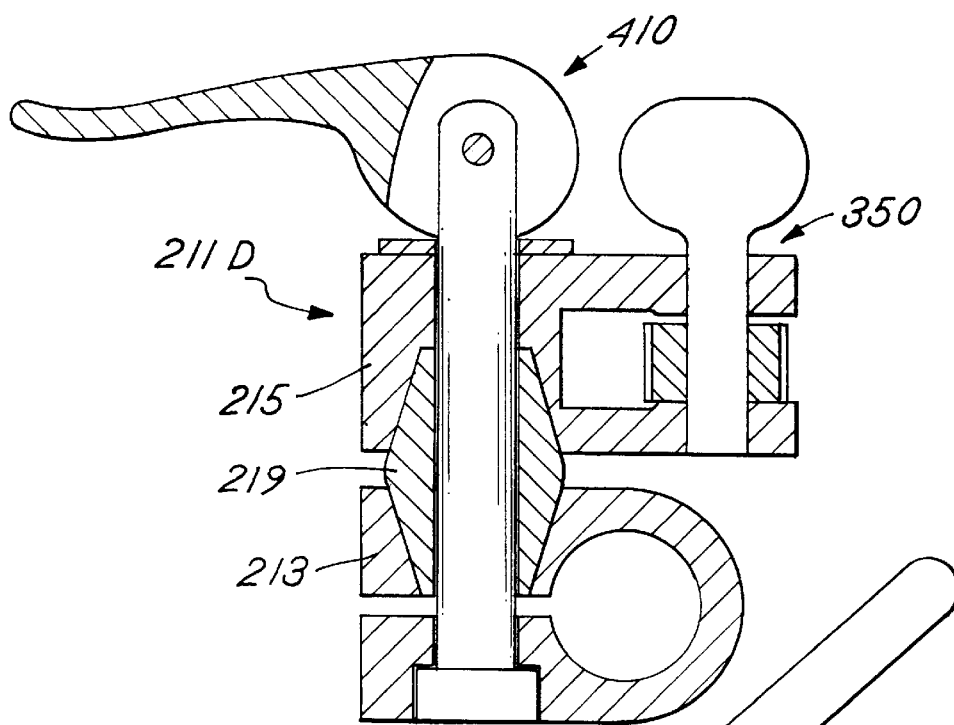
FIG. 19 is a cross-sectional side view of a fourth embodiment of a joint clamp for use in the retraction system of FIG. 1.

Referring now to FIG. 19, the joint clamp 211D of the fourth embodiment utilizes quick release mechanism 410 in connection with rachet member 215 and clamp member 213 joined about wedge member 219. As will suggest itself, wedge member 219 can be replaced with sets of locking teeth 214*a*, 214*b* as are shown in FIGS. 13–18. The rachet member 215 shown in FIG. 19 includes a crank mechanism 350; however, a rachet member such as the one described and shown in FIGS. 7 and 8 can also be used. For an understanding of this fourth embodiment, reference is made to the above discussion of FIGS. 7–18 which provides a detailed description of all components used in the fourth embodiment.

Figure 21:
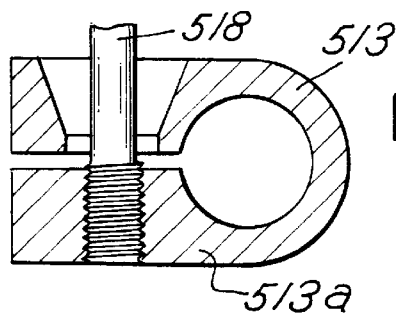
FIG. 21 is a partial side view of an adjustable stop means for use with the disclosed joint clamps.

Referring to FIGS. 21–26, alternate embodiments of the joint clamp of FIG. 20 are shown in detail. FIG. 21 shows an alternative method of attaching the shaft 518 to the second clamping member 513. The shaft 518 threadably engages a first leg 513*a* of a clamping member 513 allowing a user to adjust the length of the shaft 518 that engages the threads of leg 513*a*. By turning the threaded shaft 518, the useful length of shaft 518 can be shortened or lengthened, respectively increasing or decreasing the clamping force provided by the joint clamping members.

Figure 22:
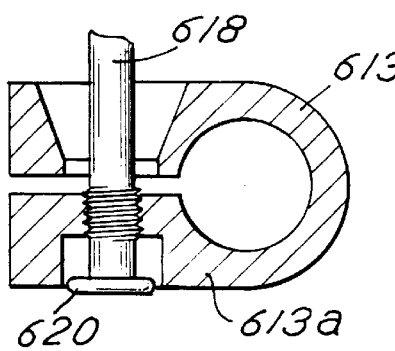
FIG. 22 is a partial side view of an adjustable stop means for use with the disclosed joint clamps.
Figure 26:
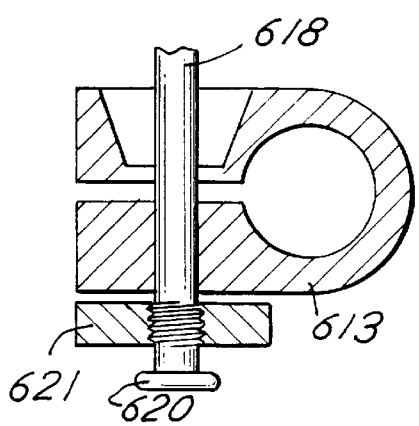
FIG. 26 is a partial side view of an adjustable stop means for use with the disclosed joint clamps.

FIG. 22 shown an alternate embodiment of the joint clamp detail of FIG. 21 that prevents removal of the shaft member 618. In FIG. 22, the shaft member 618 is maintained in contact with the other components of the assembly by a flathead screw 620. The inner threads of joint clamp 613 prevent the joint clamp 613 from passing beyond the head of the flathead screw 620, thus, maintaining the entire assembly as a single piece. Dowel pin 421 and flathead screw 620 serve as a pair of stops which maintain all of the components as a single unit structure. As a result, joint clamp 410 cannot be taken apart. Therefore, after cleaning, the joint clamp does not require reassembly during surgery. It merely requires the rotation of the cam lever 432. As will suggest itself, means other than dowel pin 421 and flathead screw 620 can be used to provide stops for the joint clamp. In addition, as shown in FIG. 26, shaft member 618 may threadably engage a separate stop member 621, rather than a threaded leg 613*a* of the clamping member 613 in order to provide the necessary clamping force.

Figure 23:
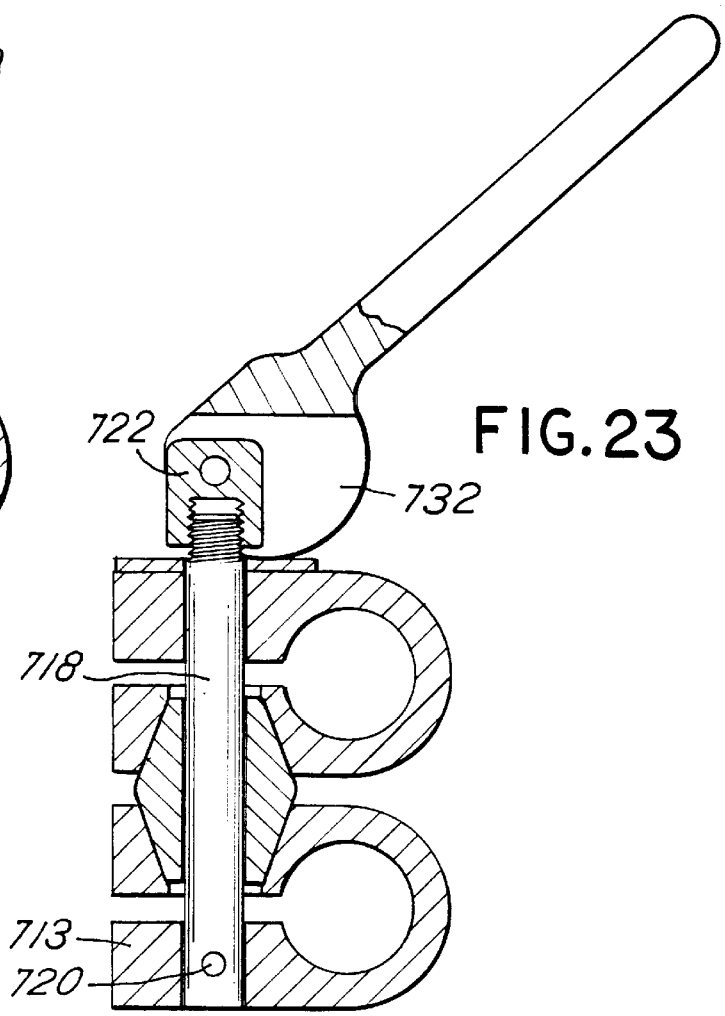
FIG. 23 is a cross-sectional side view of a sixth embodiment of a joint clamp for use in the surgical retractor system of FIG. 1.

FIG. 23 depicts an alternate embodiment of the universal joint clamp of FIG. 20. Here, dowel pin 720 attaches the shaft 718 to the second clamping member 713. The cam member 732 includes a threaded portion 722 for engaging a second set of threads disposed along a segment near the top of the shaft 718. Threadably engaging the shaft 718 and the cam member 732 allows the user to selectively adjust the clamping force of the respective clamping members. This is achieved by varying the distance between the two stop members—in this case, dowel pin 720 and the threaded portion 722 of the cam head 732.

Figure 24:
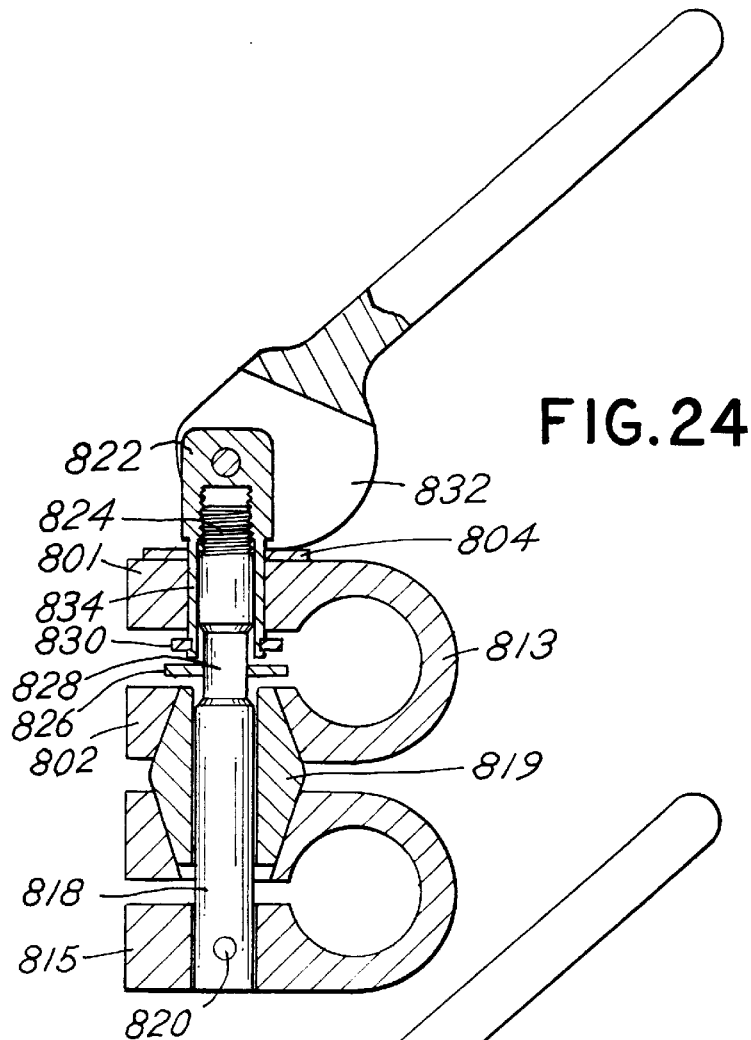
FIG. 24 is a cross-sectional side view of a seventh embodiment of a joint clamp for use in the surgical retractor system of FIG. 1.

FIG. 24 shows a variation of the cam tightened universal joint clamp of FIG. 23. Dowel pin 820 secures the shaft 818 to the second clamping member 815. The cam member 832 includes a threaded portion 822 adapting to engage a second set of threads disposed along a segment 824 near the top of the shaft 818. Threadably engaging the shaft 818 and the cam member 832 allows the user to selectively adjust the clamping force of the respective clamping members.

The threaded portion 822 of cam member 832 includes a necked down section 834 that extends through the aperture of the first leg 801 of clamping member 813. A retaining ring 830 engages an annular recess in the section 834 securing the cam member 832 in a rotatable manner to the clamping member 813. A friction ring 804 is disposed between the cam member 832 and the first clamping member 813.

The shaft 818 includes a necked down segment 828. A second retaining ring 826 is disposed between the first leg 801 and the second leg 802 of the first clamping member 813. When the threaded portion 824 of the shaft 818 is disengaged from the cam member 832, the retaining ring 826 slides along segment 828 of the shaft 818 separating the threads of the cam 832 and the shaft 818 to allow for cleaning, lubricating and sterilizing of all components. Retaining ring 826 also acts upon the shaft 818 and the second leg 802 of the first clamping member 813 to maintain the components 813, 819, 815 as a single unit structure. Another retaining ring 830 acts upon the first leg 801 of the first clamping member 813 to maintain components 832, 813 as a single unit structure, thereby making the entire assembly a single unit via the leg portions 801, 802 of the first clamping member 813.

Figure 25:
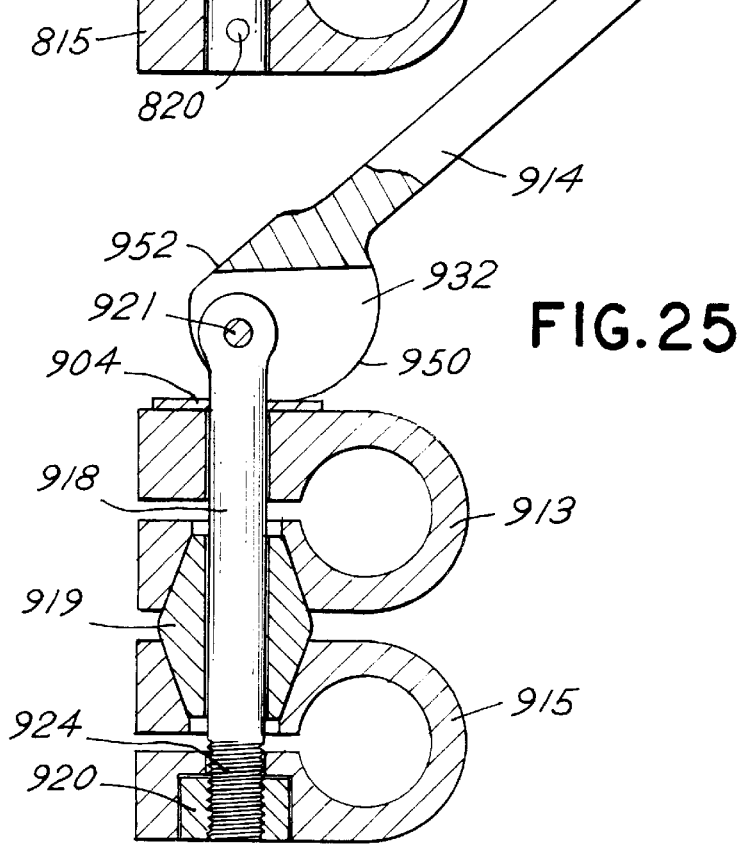
FIG. 25 is a cross-sectional side view of an eighth embodiment of a joint clamp for use in the surgical retractor system of FIG. 1.

Referring to FIG. 25, an adjustable cam tightened universal joint of the present invention is shown. The shaft 918 has a threaded segment 924 near one end. The threaded segment 924 engages a circular nut 920 for securing the components 913, 919, 915 along the shaft 918. In this particular embodiment, the nut 920 can be adjusted during assembly, then fixed in position by a weld, solder, adhesive or other securing means. Securing the nut 920 to the shaft 918 maintains the entire assembly 904, 913, 919, 915 as a single unit. Preferably, the nut 920 would be circular to enable the cam handle 914 to be rotated about the axis of the shaft 918 in any direction.

The universal joint includes a self-lubricating washer 904 disposed between the cam member 932 and the first clamping member 913. Suitable materials for the washer include Teflon, Raydel, Celcon, and Nitronic 60 SS, although many other materials readily present themselves.

The cam surface 950 includes a flat segment 952. The flat segment 952 allows movement of the components 904, 913, 919, 915 along the shaft 918 when the cam handle 914 is positioned such that the flat segment 952 is between the dowel pin 921 and washer 904. Movement of the components along the shaft 918 allows access for cleaning without disassembly of the entire unit.

While particular embodiments of the invention have been shown, it will be understood that the invention is not limited thereto since modifications may be made by those skilled in the art, particularly in light of the forgoing teaching. It is, therefore, the appended claims which define the true spirit and scope of the invention.

We claim:

1. A clamping apparatus for use in a surgical retractor system, the apparatus comprising:

a shaft member having first and second ends and a shaft axis running concentrically through the shaft member;

a first clamping member mounted on the shaft member, the first clamping member having leg portions movable toward and away from each other between a clamping and non-clamping position;

a second clamping member mounted on the shaft member, the second clamping member having leg portions movable toward and away from each other between a clamping and non-clamping position;

a cam member pivotally engaging the first end of the shaft member for rotation about a pivot axis perpendicular to the shaft axis of the shaft member, the cam member having a cam with an outer surface of incrementally increasing radius from the pivot axis whereby rotation of the cam member about the pivot axis generates a clamping force urging the leg portions of the first and second clamping members between the clamping and non-clamping positions, the cam member rotatable 360 degrees about the axis of the shaft whereby the cam member may be placed at any position about the axis of the shaft relative to only one of the clamping members for rotation into the clamping positions.

2. The clamping apparatus of claim 1 wherein the cam member further includes a lever arm connected to the cam to facilitate the rotation of the cam member between the clamping and the non-clamping positions.

3. The clamping apparatus of claim 1 further including a stop member positioned at said second end of said shaft.

4. The clamping apparatus of claim 1 wherein the second clamping member is non-rotationally attached to the shaft member.

* * * * *